(12) United States Patent
Mori et al.

(10) Patent No.: US 7,973,070 B2
(45) Date of Patent: Jul. 5, 2011

(54) MONATIN HYDRATE CRYSTALS

(75) Inventors: Kenichi Mori, Kawasaki (JP); Eriko Ono, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 86 days.

(21) Appl. No.: 12/401,997

(22) Filed: Mar. 11, 2009

(65) Prior Publication Data

US 2009/0318528 A1      Dec. 24, 2009

Related U.S. Application Data

(60) Provisional application No. 61/119,396, filed on Dec. 3, 2008, provisional application No. 61/036,349, filed on Mar. 13, 2008.

(30) Foreign Application Priority Data

Mar. 11, 2008  (JP) ................................ 2008-060859
Dec. 2, 2008   (JP) ................................ 2008-307637

(51) Int. Cl.
    A61K 31/405    (2006.01)
    C07D 209/04    (2006.01)

(52) U.S. Cl. ...................................... 514/419; 548/491

(58) Field of Classification Search .................. 514/419; 548/491

See application file for complete search history.

(56) References Cited

U.S. PATENT DOCUMENTS

| | | |
|---|---|---|
| 105,696 A | 6/1909 | Kawahara et al. |
| 7,064,219 B2 | 6/2006 | Kawahara et al. |
| 7,241,599 B2 | 7/2007 | Sugiyama et al. |
| 7,244,462 B2 | 7/2007 | Amino et al. |
| 7,297,800 B2 | 11/2007 | Sugiyama et al. |
| 7,329,427 B2 | 2/2008 | Amino et al. |
| 7,351,569 B2 | 4/2008 | Sugiyama et al. |
| 7,371,549 B2 | 5/2008 | Sugiyama et al. |
| 7,390,909 B2 | 6/2008 | Kawahara et al. |
| 7,396,941 B2 | 7/2008 | Mori et al. |
| 7,402,412 B2 | 7/2008 | Sugiyama et al. |
| 7,432,100 B2 | 10/2008 | Sugiyama et al. |
| 7,534,590 B2 | 5/2009 | Mori et al. |
| 7,534,898 B2 | 5/2009 | Amino et al. |
| 7,553,974 B2 | 6/2009 | Mori et al. |
| 7,612,214 B2 * | 11/2009 | Amino et al. ................ 548/495 |
| 7,662,596 B2 | 2/2010 | Sugiyama et al. |
| 7,678,925 B2 | 3/2010 | Kawahara et al. |
| 7,781,005 B2 | 8/2010 | Mori |
| 7,795,296 B2 * | 9/2010 | Amino et al. ................ 514/419 |
| 2005/0137246 A1 | 6/2005 | Amino et al. |
| 2005/0272939 A1 | 12/2005 | Amino et al. |
| 2006/0009394 A1 | 1/2006 | Amino |
| 2006/0014819 A1 | 1/2006 | Mori et al. |
| 2006/0083695 A1 | 4/2006 | Mori |
| 2007/0066832 A1 | 3/2007 | Mori et al. |
| 2007/0072277 A1 | 3/2007 | Sugiyama et al. |
| 2007/0191464 A1 | 8/2007 | Amino et al. |
| 2008/0193975 A1 | 8/2008 | Sugiyama et al. |
| 2008/0193984 A1 | 8/2008 | Sugiyama et al. |
| 2008/0199921 A1 | 8/2008 | Sugiyama et al. |
| 2008/0207920 A1 | 8/2008 | Kawahara et al. |
| 2008/0318290 A1 | 12/2008 | Sugiyama et al. |
| 2009/0259052 A1 | 10/2009 | Kawahara et al. |
| 2009/0318528 A1 | 12/2009 | Mori et al. |
| 2010/0105924 A1 | 4/2010 | Kawahara et al. |
| 2010/0184165 A1 | 7/2010 | Sugiyama et al. |

FOREIGN PATENT DOCUMENTS

| | | |
|---|---|---|
| EP | 1 449 832 | 8/2004 |
| EP | 1 533 300 | 5/2005 |
| EP | 1 582 514 | 10/2005 |
| EP | 1 719 758 | 11/2006 |

OTHER PUBLICATIONS

Office Action issued in European Patent Application No. 09250672.4 on Oct. 1, 2010.
U.S. Appl. No. 12/825,886, filed Jun. 29, 2010, Amino, et al.
U.S. Appl. No. 12/768,360, filed Apr. 27, 2010, Sugiyama, et al.
U.S. Appl. No. 12/108,889, filed Apr. 24, 2008, Sugiyama, et al.
U.S. Appl. No. 12/758,433, filed Apr. 12, 2010, Sugiyama, et al.
U.S. Appl. No. 12/613,839, filed Nov. 6, 2009, Sugiyama, et al.
U.S. Appl. No. 07/178,323, filed Apr. 6, 1988, Amino, et al.

* cited by examiner

*Primary Examiner* — Yong Chu
(74) *Attorney, Agent, or Firm* — Oblon, Spivak, McClelland, Maier & Neustadt, L.L.P.

(57) ABSTRACT

New (2R,4R) monatin monosodium salt hydrate crystals characterized by having specific characteristic X-ray diffraction peaks provide general-purpose, stable, and safe monatin sodium salt crystals incorporating no organic solvent. These crystal may be prepared by a method that requires no organic solvent in the crystallization, separation, and drying steps. These crystal are useful as sweeteners and for the preparation of orally consumed products, such as foods, beverages, pharmaceutical products, topical pharmaceutical products, and feeds containing general-purpose, stable, and safe monatin sodium salt crystals.

31 Claims, 6 Drawing Sheets

[Fig. 1]
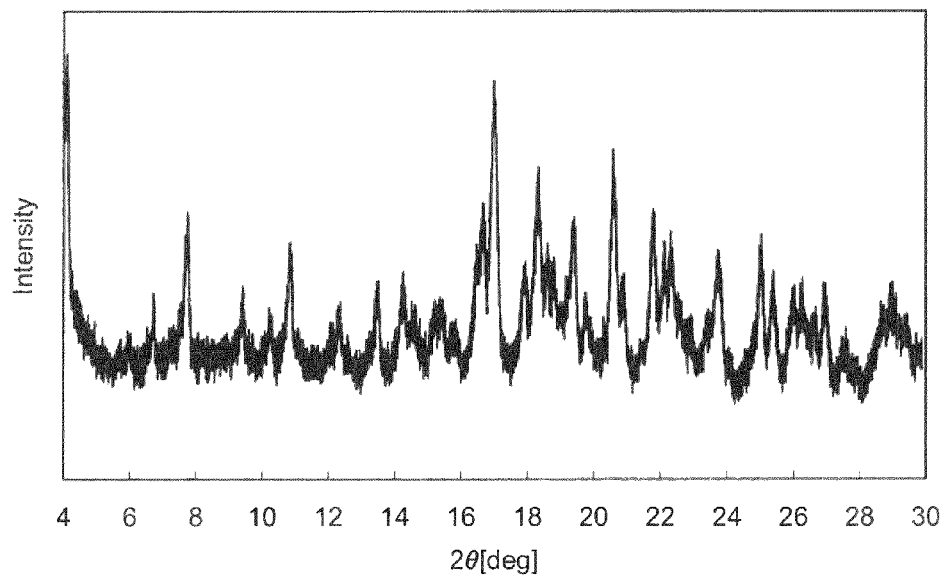
[Fig. 2]
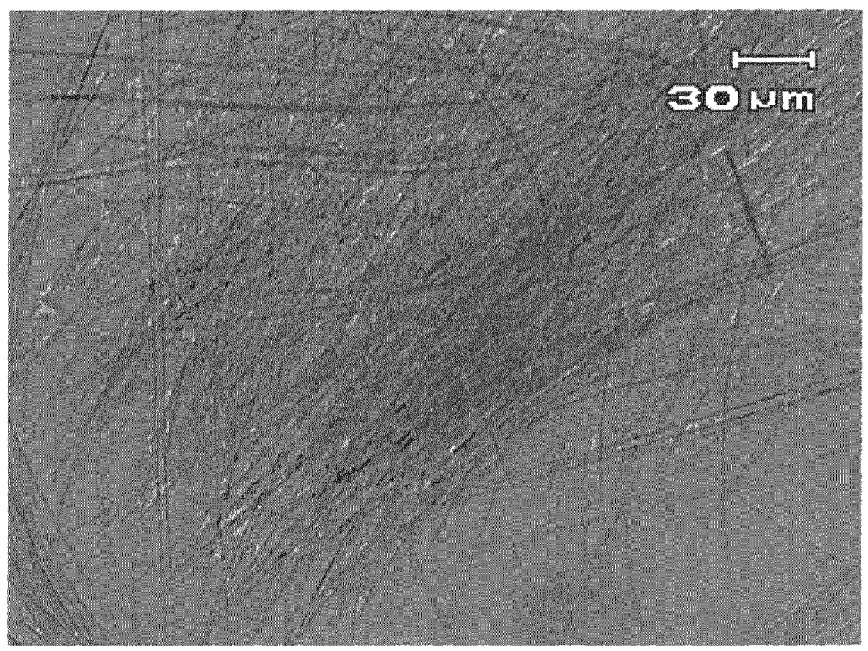

[Fig. 3]
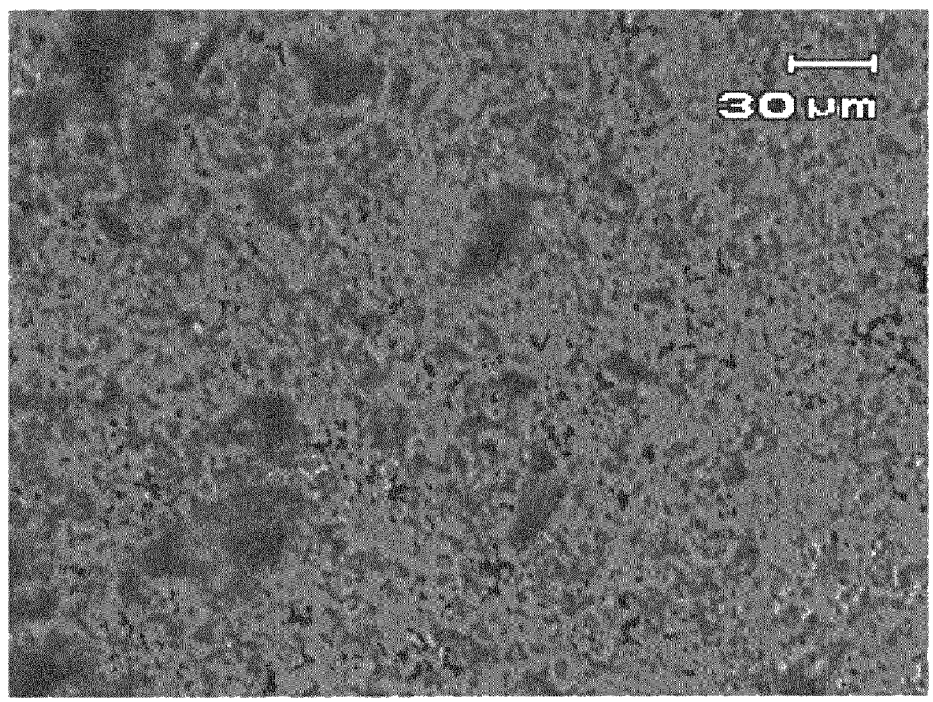

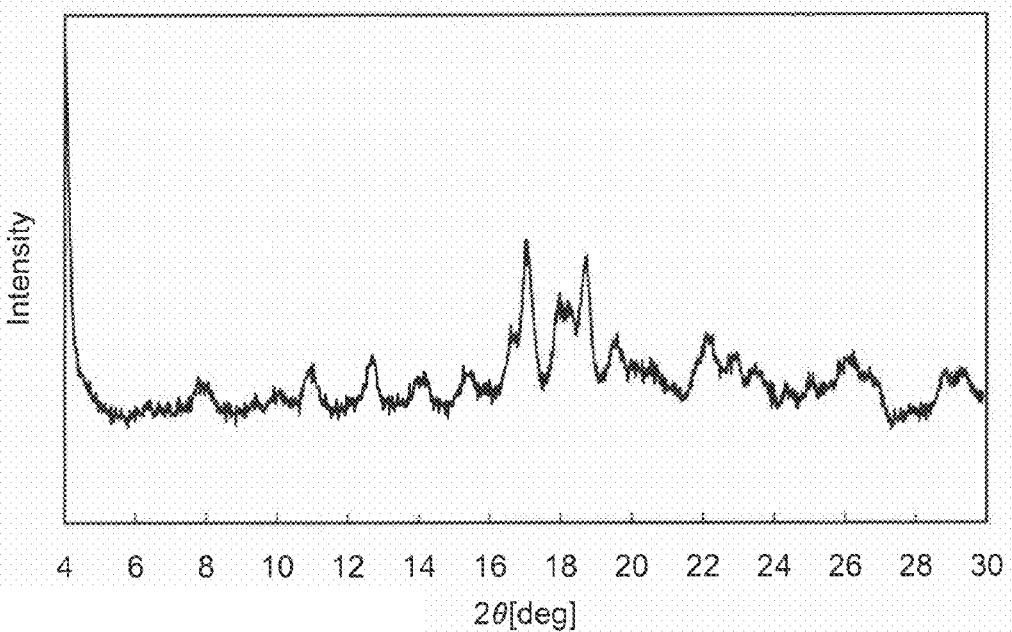
[Fig. 4]

[Fig. 5]
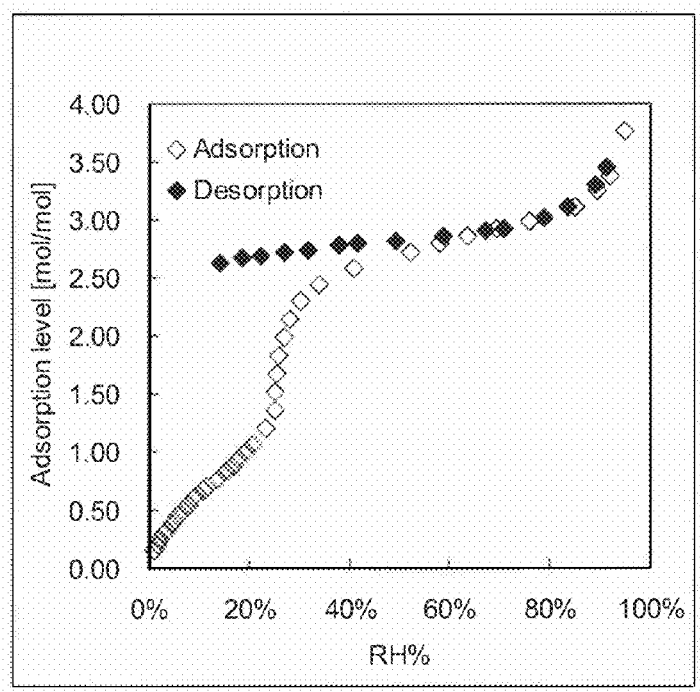
[Fig. 6]
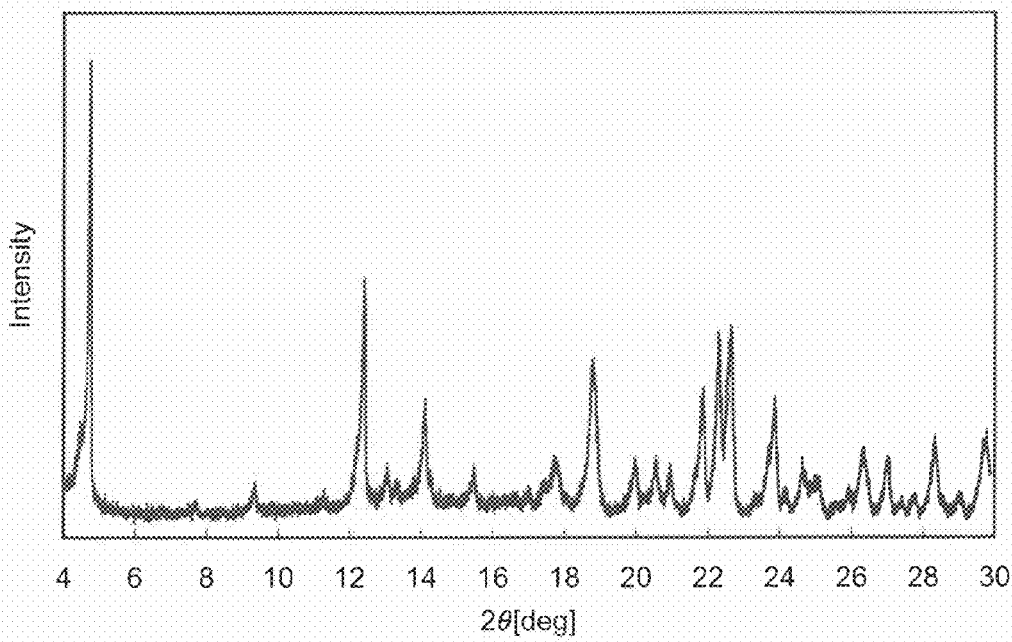

[Fig. 7]
[Fig. 8]
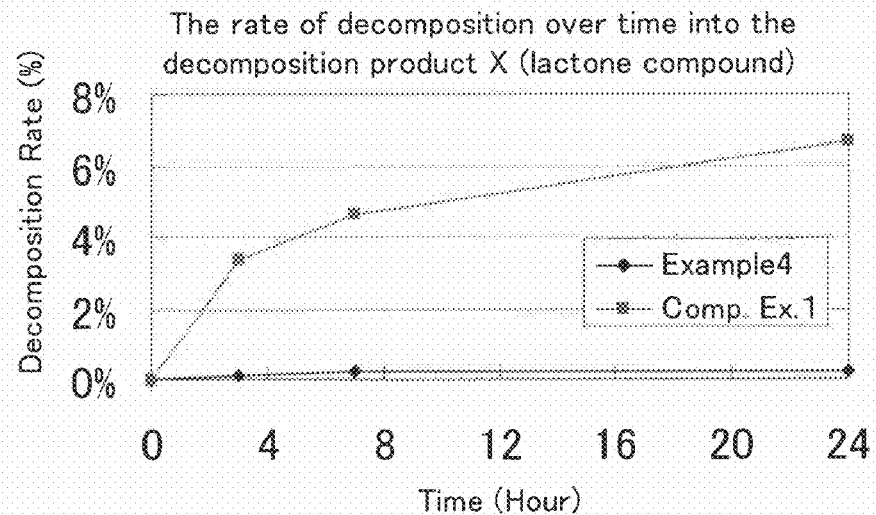

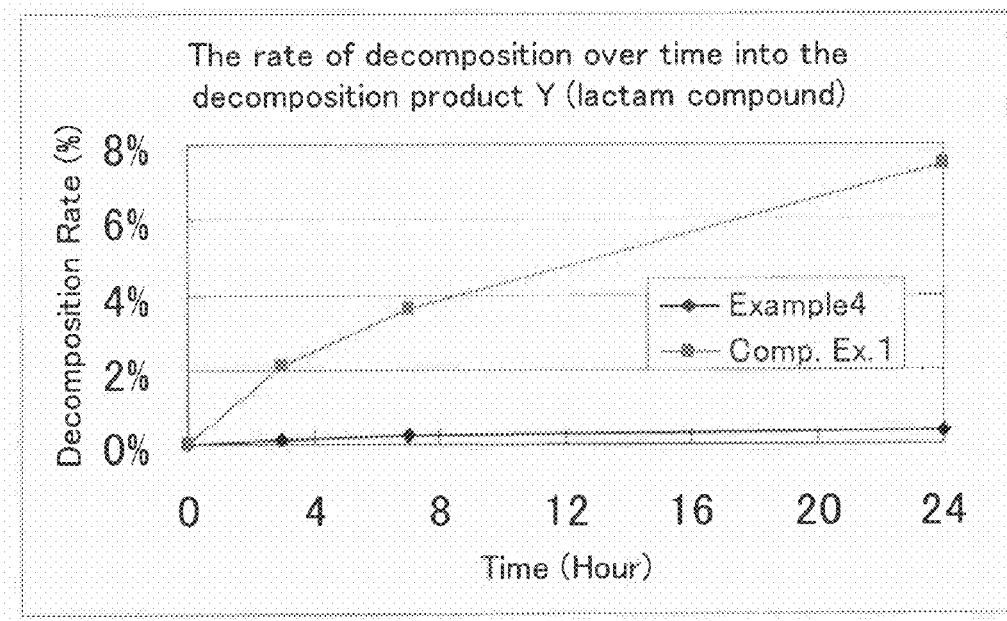
[Fig. 9]

MONATIN HYDRATE CRYSTALS

CROSS REFERENCES TO RELATED APPLICATIONS

This application claims priority to U.S. Provisional Patent Application No. 61/036,349, filed on Mar. 13, 2008; U.S. Provisional Application No. 61/119,396, filed on Dec. 3, 2008; Japanese Patent Application No. 060859/2008, filed on Mar. 11, 2008; and Japanese Patent Application No. 307637/2008, filed on Dec. 2, 2008, all of which are incorporated herein by reference in their entireties.

BACKGROUND OF THE INVENTION

1. Field of the Invention

The present invention relates to new (2R,4R) monatin monosodium salt hydrate crystals, characterized by having specific, characteristic X-ray diffraction peaks. It also relates to monatin crystals comprising these crystals, and to orally consumed products comprising these crystals.

2. Discussion of the Background

Monatin is a naturally occurring amino acid derivative isolated from the bark of the roots of *Schlerochiton ilicifolius*, which is a plant naturally grown in the area of northern Transvaal of South Africa. The structure of monatin was reported to be (2S,4S)-2-amino-4-carboxy-4-hydroxy-5-(3-indolyl)-pentanoic acid ((2S,4S)-4-hydroxy-4-(3-indolylmethyl)-glutamic acid) by R. Vleggaar et al. (see, R. Vleggaar et al., *J. Chem. Soc. Perkin Trans.*, 3095-3098 (1992)). The intensity of the sweet taste of the (2S,4S) substance (natural-type monatin) derived from the natural plant is reported in R. Vleggaar et al., *J. Chem. Soc. Perkin Trans.*, 3095-3098 (1992) to be 800 to 1,400-fold that of sucrose. Although various methods of synthesizing monatin have been reported, many of these relate to methods of synthesizing a mixture of stereoisomers. There have been almost no reports in which each of four stereoisomers having the same chemical structural formulae as natural-type monatin is synthesized and isolated as a pure substance and the properties thereof are investigated in detail (see, ZA 87/4288; ZA 88/4220; U.S. Pat. No. 5,994,559; Holzapfel et al., *Synthetic Communications*, vol. 24 (22), 3197-3211 (1994); and K. Nakamura et al., *Organic Letters*, 2, 2967-2970 (2000)).

A number of studies have been conducted in recent years into methods of manufacturing monatin (see, WO 2003-056026 and WO 2003-059865). A certain amount of information has been reported on monatin crystals, but much of this relates to potassium salts. There have been only limited reports on sodium salts, which are of the greatest general utility (see, WO 2003-045914, U.S. Published Patent Application No. 2005-272939, Japanese Patent Application Publication No. 2005-154291, and Japanese Patent Application Publication No. 2006-052213). The crystals of the characteristic existing (2R,4R) monatin sodium salt are fine, the salt is difficult to handle, and its thermal stability is somewhat lacking (see, WO 2003-045914).

SUMMARY OF THE INVENTION

Accordingly, it is one object of the present invention to provide novel crystals of (2R,4R) monatin monosodium salt.

It is another object of the present invention to provide novel, stable (2R,4R) monatin sodium salt crystals.

It is another object of the present invention to provide novel, stable (2R,4R) monatin sodium salt hydrate crystals.

It is another object of the present invention to provide novel monatin crystals which contain such crystals of (2R,4R) monatin monosodium salt hydrate.

It is another object of the present invention to provided novel orally consumed products which contain such these crystals.

It is another object of the present invention to provide novel uses of such crystals as sweeteners.

It is another object of the present invention to provide orally consumed products such as foods, beverages, pharmaceutical products, topical pharmaceutical products, and feeds which containing general-purpose, stable, and safe new sodium salt crystals of (2R,4R) monatin.

These and other objects, which will become apparent during the following detailed description, have been achieved by the inventors' obtaining new (2R,4R) monatin monosodium salt hydrate crystals characterized by having specific characteristic X-ray diffraction peaks, and discovered that the above problems were solved by these crystals.

Thus, the present invention provides:

(1) (2R,4R) Monatin monosodium salt hydrate crystals, characterized by having characteristic X-ray diffraction peaks at angles of diffraction (2θ±0.2°, CuKα) of either:
group (A) 7.7°, 10.9°, 16.7°, and 17.0°; or
group (B) 4.7°, 12.4°, 18.8°, and 22.6°.

(2) Monatin crystals characterized by having characteristic X-ray diffraction peaks at angles of diffraction (2θ±0.2°, CuKα) of either:
group (A) 7.7°, 10.9°, 16.7°, and 17.0°; or
group (B) 4.7°, 12.4°, 18.8°, and 22.6°.

(3) Monatin crystals, which comprise (2R,4R) monatin monosodium salt hydrate crystals according to (1).

(4) The monatin crystals according to (2) or (3), wherein the enantiomer excess rate of the (2R,4R) monatin monosodium salt hydrate crystals is 10 to 100% ee.

(5) The monatin crystals according to (2) or (3), wherein the diastereomer excess rate of the (2R,4R) monatin monosodium salt hydrate crystals is 10 to 100% de.

(6) The monatin crystals according to (2) or (3), wherein the sweetness intensity thereof is 200-fold or more that of a 5 percent sucrose aqueous solution.

(7) The monatin crystals according to (2) or (3), wherein the chemical purity thereof is 50 to 100 weight percent.

(8) An orally consumed product, characterized by comprising the (2R,4R) monatin monosodium salt hydrate crystals according to (1).

(9) An orally consumed product, characterized by comprising the monatin crystals of any one of (2) to (7).

The new (2R,4R) monatin monosodium hydrate crystals characterized by having specific characteristic X-ray diffraction peaks make it possible to provide stable monatin sodium salt crystals. They also make it possible to clarify the utility and various physical properties of these stereoisomers as sweeteners. And they make it possible to provide orally consumed products such as foods, beverages, pharmaceutical products, topical pharmaceutical products, and feeds containing general-purpose, stable, and safe monatin sodium salt crystals. This invention can also be applied to (2S,4S) monatin, of course.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 is a powder X-ray diffraction chart of (2R,4R) monatin monosodium salt hydrate crystals (A) after drying (Example 1).

FIG. 2 is an optical microphotograph of (2R,4R) monatin monosodium salt hydrate crystals (A) immediately prior to separation from a crystallized solution (200-fold magnification) (Example 1).

FIG. 3 is an optical microphotograph of (2R,4R) monatin monosodium salt hydrate crystals (A) following drying and pulverizing in a mortar (200-fold magnification)(Example 1).

FIG. 4 is a powder X-ray diffraction chart of (2R,4R) monatin monosodium salt hydrate crystals (A) after a redrying test (Example 2).

FIG. 5 is the plot of a water vapor adsorption/desorption curve for (2R,4R) monatin monosodium salt hydrate crystals (A) (Example 3).

FIG. 6 is a powder X-ray diffraction chart of (2R,4R) monatin monosodium salt monohydrate crystals (B) after drying (Example 4).

FIG. 7 is an optical microphotograph of (2R,4R) monatin monosodium salt monohydrate crystals (B) immediately prior to separation from a crystallized solution (200-fold magnification) (Example 4).

FIG. 8 is a plot of the rate of decomposition over time into the decomposition product X (lactone compound) of Example 4 and Comparative Example 1.

FIG. 9 is a plot of the rate of decomposition over time into the decomposition product Y (lactam compound) of Example 4 and Comparative Example 1.

DETAILED DESCRIPTION OF THE PREFERRED EMBODIMENTS

The present invention relates to new (2R,4R) monatin monosodium salt hydrate crystals characterized by having specific characteristic X-ray diffraction peaks.

In the present invention, the term "natural-type monatin" refers to the (2S,4S) form of the stereo structure. All compounds having the same chemical structural formula are collectively referred to as "monatin." Accordingly, the term "non-natural-type stereoisomers of monatin" refers to "stereoisomers of natural-type monatin," "non-natural-type monatin," "(2S,4R) monatin," "(2R,4S) monatin," "(2R,4R) monatin," and the like. Monatin ((2S,4S) form) is included with these stereoisomers by referring to "the four stereoisomers," and in particular, the natural form of monatin is referred to as "(2S,4S) monatin" or "'(2S,4S) monatin' or the like."

The (2R,4R) monatin employed in the present invention can be prepared by known methods; the method employed is not limited. For example, it can be enzymatically obtained from tryptophan via indolepyruvic acid (see, WO 2003-056026), or obtained from tryptophan, passing via indolepyruvic acid, by reduction from an oxime (see, WO 2003-059865). In the manufacturing process, the natural-type monatin (2S,4S) form and the non-natural-type stereoisomer (2S,4R) and (2R,4S) forms can be contained in addition to (2R,4R) monatin.

The monatin thus obtained may be employed as a mixture containing the four isomers of monatin, or may be separated and purified for use by known methods, such as with adsorption resin or ion-exchange resin. Generally, it can be incorporated as a free compound, ammonium salt, potassium salt, basic amino acid salt, or some other known salt. The method of obtaining an aqueous solution containing a high concentration of monatin monosodium salt is not specifically limited. Free compounds and salts of monatin obtained in the form of sodium salts by neutralization or salt exchange, as well as those obtained by salt exchange by means of an ion-exchange resin, can be employed. When an even higher concentration is required, a known method such as solvent distillation under reduced pressure can be employed.

The sodium employed in the present invention is not specifically limited. It can be derived from inorganic sodium compounds such as sodium hydroxide, sodium carbonate, sodium bicarbonate, and sodium iodide, as well as from organic sodium compounds such as sodium acetate, sodium oxalate, and sodium lactate, by various methods such as neutralization and salt exchange. These may be employed separately, or in combinations of two or more.

Methods of precipitating the (2R,4R) monatin monosodium salt hydrate crystals of the present invention that have the characteristic X-ray peaks of (A) 7.7°, 10.9°, 16.7°, and 17.0° (also abbreviated hereinafter to (2R,4R) monatin monosodium salt hydrate crystals (A) or (2R,4R) monatin monosodium hydrate crystals (A)) will be described.

Allowing an aqueous solution containing a high concentration of (2R,4R) monatin monosodium salt to stand or subjecting it to stirring precipitation will cause the crystals to precipitate out. Sowing seed crystals of (2R,4R) monatin monosodium salt hydrate is desirable because it promotes stable and efficient precipitation.

The precipitating crystals can be readily obtained as wet crystals by subjecting them to a separation process such as filtration. Washing the crystals is not specifically limited, so long as a crystal-solvent exchange is not induced; water can be employed. So long as a crystal solvent exchange is not induced, a water-miscible solvent, such as methanol, ethanol, n-propanol, isopropanol, n-butanol, t-butanol, sec-butanol, propylene glycol, acetonitrile, or THF; inorganic salts; and the like can be incorporated. Since the precipitation yield is higher when no crystal-solvent exchange is induced, washing with water alone is desirable, washing with cold water is preferred, washing with 0 to 20° C. cold water is of greater preference, washing with 0 to 15° C. cold water is of even greater preference, washing with 0 to 10° C. cold water is of still greater preference, and washing with 0 to 5° C. cold water is of particular preference.

The wet crystals thus obtained can be subjected to a known drying process to derive dry crystals. The drying equipment employed in the drying process is not specifically limited. A temperature range that does not melt the (2R,4R) monatin monosodium salt can be employed. Drying under reduced pressure, drying under an airflow, hot blow-drying, and the like can be employed.

The (2R,4R) monatin monosodium salt hydrate crystals thus obtained are acicular and have characteristic X-ray diffraction peaks at angles of diffraction (2θ±0.2°, CuKα) of 7.7°, 10.9°, 16.7°, and 17.0°.

The (2R,4R) monatin monopotassium salt monohydrate crystals described in Example 17 of WO 2003-045914 have a solid crystalline shape. In contrast to these (2R,4R) monatin monopotassium salt monohydrate crystals, which cannot be mixed into a quality powder with an excipient without a pulverizing step, the (2R,4R) monatin monosodium salt hydrate crystals (A) of the present invention, even when mixed as is into a powder with an excipient, are characterized by yielding a sweetener composition producing a good taste sensation without creating a gritty sensation on the tip of the tongue, affording good mouth feel, and having a good initial sweetness that are of the same quality as those of granulated sugar.

In a water vapor adsorption/desorption test of (2R,4R) monatin monosodium salt hydrate crystals (A), the trihydrate exhibited the greatest stability. However, the crystalline structure is thought to have the singular property of gradually losing water of crystallization as is. Although the crystalline lattice that is formed by (2R,4R) monatin monosodium salt and trihydrate is itself rigid, perhaps because the hydrogen bonds of the water of crystallization that is present within it are relatively loose, the crystalline lattice is thought to have the property of being able to gradually lose its water of crystallization under the effect of just a vacuum pump at 40° C. or the like. Accordingly, despite identical characteristic X-ray diffraction peaks, it can be denoted as (2R,4R) monatin monosodium salt n-hydrate crystals (n=0.1 to 3.0). That is, when referred to as (2R,4R) monatin monosodium salt hydrate crystals (A), what is meant in a narrow sense is (2R,4R) monatin monosodium salt trihydrate crystals, and what is meant in a broad sense is (2R,4R) monatin monosodium salt n-hydrate crystals (n=0.1 to 4.0).

The differences between the (2R,4R) monatin monosodium salt hydrate crystals (A) of the present invention and the (2R,4R) monatin monosodium salt crystals of Examples 14 and 20 in WO 2003-045914 will be examined. The crystals described in Example 14 of WO 2003-045914, which are (2R,4R) monatin monosodium salt 0.2 ethanolate, are described as "exhibiting characteristic X-ray diffraction peaks at diffraction angles (2θ, CuKα) of 4.4°, 15.3°, 17.5°, 19.1°, and 24.6°". The crystals described in Example 20 of WO 2003-045914, when traced, exhibit hydrates of (2R,4R) monatin monosodium salt corresponding to 2.5 hydrates. These crystals are described as "exhibiting characteristic X-ray diffraction peaks at diffraction angles (2θ, CuKα) of 4.4°, 15.2°, 17.8°, 20.6°, and 24.1°". When these are examined, once the crystals have been constructed, the fact that crystalline transition tends not to occur even once the crystal solvent has been removed is thought to be a singular property of monatins, particularly (2R,4R) monatin, or (2R,4R) monatin monosodium salt. Accordingly, in the course of obtaining the new (2R,4R) monatin monosodium salt hydrate crystals (A) having characteristic X-ray diffraction peaks at angles of diffraction (2θ±0.2°, CuKα) of 7.7°, 10.9°, 16.7°, and 17.0° of the present invention, an organic solvent capable of forming a solvate, such as ethanol, must not be present in large quantity during the crystallization stage. That is, it is desirable to employ just water during the crystallization stage, and it is preferable to employ just water during both the crystallization and washing stages.

The new (2R,4R) monatin monosodium salt hydrate crystals (A) having characteristic X-ray diffraction peaks at angles of diffraction (2θ±0.2°, CuKα) of (A) 7.7°, 10.9°, 16.7°, and 17.0° make it possible to provide general-purpose, stable, and safe monatin sodium salt crystals in which organic solvents are not incorporated. They also make it possible to provide a manufacturing method in which organic solvent is not required in either the crystallization, separation, or drying step.

The method of crystallizing those (2R,4R) monatin monosodium salt hydrate crystals having characteristic X-ray peaks at (B) 4.7°, 12.4°, 18.8°, and 22.6° among the crystals of the present invention (sometimes abbreviated hereinafter to "(2R,4R) monatin monosodium salt hydrate crystals (B)" or "(2R,4R) monatin monosodium salt monohydrate crystals (B)") will be described next.

The crystals can be precipitated by concentrating an aqueous solution containing a high concentration of (2R,4R) monatin and sodium source as mentioned above, introducing a water-miscible solvent, and allowing the mixture to stand or inducing crystallization by stirring. Specifically, water-miscible solvents in the form of lower monohydric alcohols such as methanol, ethanol, isopropanol, n-butanol, and t-butanol; ketones such as acetone and methyl ethyl ketone; and the like can be employed. Some residual water may also be present. The concentration of (2R,4R) monatin crystals in the solvent is not specifically limited so long as it is supersaturated, causing crystals to precipitate out, but 20 to 60 weight percent is desirable. From the viewpoint of achieving a solution viscosity suited to manufacturing, 30 to 50 weight percent is preferable, and 35 to 45 weight percent is of greater preference. The temperature of dissolution is not specifically limited so long as the crystals continue to dissolve; 40 to 100° C. is desirable. Allowing an aqueous solution containing a high concentration of (2R,4R) monatin and sodium source as mentioned above to stand or subjecting it to stirring precipitation will cause the crystals to precipitate out. Sowing seed crystals of (2R,4R) monatin monosodium salt hydrate is desirable because it promotes stable and efficient precipitation. The concentration of (2R,4R) monatin crystals in the solvent is not specifically limited so long as it is supersaturated, causing crystals to precipitate out, but 20 to 60 weight percent is desirable. From the viewpoint of achieving a solution viscosity suited to manufacturing, 30 to 50 weight percent is preferable, and 35 to 45 weight percent is of greater preference. The temperature of dissolution is not specifically limited so long as the crystals continue to dissolve; 40 to 100° C. is desirable.

Sowing seed crystals of (2R,4R) monatin monosodium salt monohydrate at a high crystallization starting temperature makes it possible to stably obtain the targeted crystals. From the perspective of producing the targeted crystals without dissolving the seed crystals, the crystallization starting temperature must be lower than the temperature at which the solvent exhibits solubility. Additionally, from the perspective of promoting crystal growth and obtaining large crystals, the lower limit of the crystallization starting temperature is desirably 35° C., preferably 40° C., more preferably 43° C., still more preferably 45° C., yet more preferably 48° C., and particularly preferably, 50° C. From the perspective of producing the targeted crystals without dissolving the seed crystals, the crystallization starting temperature must be lower than the temperature at which the solvent exhibits solubility. Additionally, from the perspective of promoting crystal growth and obtaining large crystals, the upper limit of the crystallization starting temperature is desirably 80° C., preferably 70° C., and more preferably, 60° C.

The crystals that precipitate can be readily obtained as wet crystals by subjecting them to a separation process such as filtration. Washing the crystals is not specifically limited, so long as a crystal solvent exchange is not induced. Specific solvents that can be employed so long as a crystal solvent exchange is not induced are water-miscible solvents, such as methanol, ethanol, n-propanol, isopropanol, n-butanol, t-butanol, sec-butanol, propylene glycol, acetonitrile, and THF; inorganic salts; and the like.

Dry crystals can be derived by subjecting the wet crystals that have thus been obtained to a known drying process. The drying equipment employed in the drying process is not specifically limited. A temperature range over which the (2R,4R) monatin monosodium salt (B) does not melt can be employed. Drying under reduced pressure, drying under an airflow, hot blow-drying, and the like can be employed.

The (2R,4R) monatin monosodium salt monohydrate crystals (B) thus obtained are acicular and have characteristic X-ray diffraction peaks at angles of diffraction (2θ±0.2°, CuKα) of 4.7°, 12.4°, 18.8°, and 22.6°.

The differences between the (2R,4R) monatin monosodium salt monohydrate crystals (B) of the present invention and the (2R,4R) monatin monosodium salt crystals of Examples 14 and 20 in WO 2003-045914 will be examined. The crystals described in Example 14 of WO 2003-045914 are (2R,4R) monatin monosodium salt 0.2 ethanolate, and when traced, start to crystallize at 20° C. or lower. They are described as "exhibiting characteristic X-ray diffraction peaks at diffraction angles (2θ, CuKα) of 4.4°, 15.3°, 17.5°, 19.1°, and 24.6°". The crystals described in Example 20 of WO 2003-045914, when traced, exhibit hydrates of (2R,4R) monatin monosodium salt corresponding to 2.5 hydrates. These crystals are described as "exhibiting characteristic X-ray diffraction peaks at diffraction angles (2θ, CuKα) of 4.4°, 15.2°, 17.8°, 20.6°, and 24.1°". When these are examined, once the crystals have been constructed, the fact that crystalline transition tends not to occur even once the crystal solvent has been removed is thought to be a singular property of monatins, particularly (2R,4R) monatin, or (2R,4R) monatin monosodium salt. Accordingly, in the course of obtaining the new (2R,4R) monatin monosodium monohydrate crystals (B) having characteristic X-ray diffraction peaks at angles of diffraction (2θ±0.2°, CuKα) of 4.7°, 12.4°, 18.8°, and 22.6° of the present invention, the above-described high crystallization starting temperature range is extremely important; this characteristic is clearly different from the crystallization starting temperature (20° C.) of the sodium salt of WO 2003-045914. As a result, different crystalline forms are obtained. The crystals are larger than has conventionally been the case, and their stability, at 20-fold or greater, is extremely high. This was a surprising discovery.

The (2R,4R) monatin monosodium salt monohydrate crystals (B) characterized by having characteristic X-ray diffraction peaks at 4.7°, 12.4°, 18.8°, and 22.6° make it possible to provide monatin sodium salt crystals that are large in crystalline shape and have good thermal stability.

The (2R,4R) monatin monosodium salt hydrate crystals of the present invention ((A) or (B)) can form monatin crystals with another monatin isomer in the form of (2S,4S) monatin monosodium salt. In that case, the enantiomer excess rate is not specifically limited. From the perspectives of having stable crystals and performing as an effective sweetener in small quantities, the enantiomer excess rate is desirably 10 to 100% ee, preferably 30 to 100% ee, more preferably 50 to 100% ee, still more preferably 70 to 100% ee, yet more preferably 90 to 100% ee, and particularly preferably, 95 to 100% ee.

The (2R,4R) monatin monosodium salt hydrate crystals of the present invention ((A) or (B)) can form monatin crystals with other monatin isomers in the form of (2S,4R) monatin monosodium salt and (2R,4S) monatin monosodium salt. The diastereomer excess rate is not specifically limited. From the perspectives of having stable crystals and performing as an effective sweetener in small quantities, the diastereomer excess rate is desirably 10 to 100% de, preferably 30 to 100% de, more preferably 50 to 100% de, still more preferably 70 to 100% de, yet more preferably 90 to 100% de, and particularly preferably, 95 to 100% de.

The (2R,4R) monatin monosodium salt hydrate crystals of the present invention ((A) or (B)) can form monatin crystals with organic and inorganic impurities. The lower limit of chemical purity of monatin crystals containing the (2R,4R) monatin monosodium salt hydrate crystals of the present invention is not specifically limited so long as crystals are formed. However, from the perspective of forming stable crystals, 50 weight percent is desirable, 60 weight percent is preferable, 70 weight percent is more preferable, 80 weight percent is still more preferable, 90 weight percent is yet more preferable, and 95 weight percent is particularly preferable.

Additionally, the upper limit of chemical purity is desirably 100 weight percent from the perspective of achieving sweetness intensity when formulated in small quantities. The "chemical purity" referred to here is the ratio of the weight of the "monatin monosodium salt hydrate crystals" to the weight of the monatin crystals as a whole. Examples of items that decrease purity are impurities (including other isomers) in the monatin itself, inorganic salts, and salts of metals other than sodium. This is not an exhaustive list of impurities.

The (2R,4R) monatin monosodium salt hydrate crystals of the present invention ((A) or (B)) can form monatin crystals with other monatin isomers in the form of (2S,4S) monatin monosodium salt, (2S,4R) monatin monosodium salt, (2R,4S) monatin monosodium salt, and other organic and inorganic impurities. The sweetness intensity of monatin crystals containing the (2R,4R) monatin monosodium salt hydrate crystals of the present invention ((A) or (B)) is not specifically limited. From the perspective of having stable crystals and being an effective sweetener in small quantities, a sweetness intensity relative to a 5 percent sucrose aqueous solution of 200-fold or greater is desirable, 500-fold or greater is preferred, 1,000-fold or greater is of greater preference, 1,500-fold or greater is of still greater preference, 2,000-fold or greater is of even greater preference, and 2,500-fold or greater is of particular preference.

Additional sweeteners (excluding monatins and their salts) can be combined with monatin crystals containing the (2R,4R) monatin monosodium salt hydrate crystals of the present invention ((A) or (B)) of the present invention to obtain sweetening compositions. These sweeteners are not specifically limited. Specific examples are monosaccharides such as xylose, glucose, and fructose; disaccharides such as sucrose, lactose, and maltose; oligosaccharides such as fructooligosaccharides, maltooligosaccharides, isomaltooligosaccharides, and galactooligosaccharides; sugar alcohols such as xylitol, lactitol, sorbitol, erythritol, mannitol, maltitol, reduced palatinose, and reduced starch saccharification products; and high-intensity sweeteners (HIS) such as aspartame, acesulfame-K, sucralose, saccharin, stevioside, neotame, sodium cyclohexylsulfamate, stevia, glycyrrhizin, monellin, thaumatin, dulcin, brazzein, neoculin, and MHPPAPM (N-[N-[3-(3-hydroxy-4-methoxyphenyl)propyl]-L-α-aspartyl]-L-phenylalanine 1-methylester monohydrate (Advantame (CAS No. 714229-20-6)). These may be employed singly, or in combinations of two or more. From the perspective of achieving a synergistic sweetening effect, aspartame, acesulfame-K, sucralose, saccharin, sodium cyclohexylsulfamate, stevioside, and neotame are desirable; aspartame, acesulfame-K, sucralose, saccharin, stevioside, and neotame are preferable; aspartame, acesulfame-K, sucralose, stevioside, and neotame are of greater preference; aspartame, acesulfame-K, sucralose, and neotome are of even greater preference; aspartame, acesulfame-K, and sucralose are of still greater preference; and aspartame and sucralose are of particular preference. From the perspectives of quality of flavor and achieving a synergistic sweetening effect, aspartame is of particular preference.

In addition to various food materials, various additives that can be employed in orally consumed products, such as foods, beverages, pharmaceuticals, topical pharmaceutical products, and feeds, can be employed to a degree that does not impede the effect of the present invention. Specific examples are excipients in the form of dextrins such as dextrin, maltodextrin, starch decomposition products, reduced starch decomposition products, cyclodextrin, and hard-to-digest dextrins, and in the form of polysaccharides such as crystalline cellulose and polydextrose; pH regulating agents such as citric acid, phosphoric acid, lactic acid, malic acid, tartaric acid, gluconic acid, and salts thereof; antioxidants such as L-ascorbic acid, erysorbic acid, and tocopherol (vitamin E); quality-enhancing agents such as sodium acetate, glycine, glycerine fatty acid esters, and lysozyme; preservatives such as sodium benzoate and potassium sorbate; stabilizers such as pectin, gum arabic, carageenan, soy polysaccharides, and hydroxypropyl cellulose (HPC); thickening stabilizers such as xanthan gum, locust bean gum, guar gum, tamarind gum, and caraya gum; anticaking agents such as calcium phosphate, calcium carbonate, magnesium carbonate, silicon dioxide, and shell calcium; fragrances in the form of natural fragrance materials such as cinnamon oil, lemon oil, mint oil, orange oil, and vanilla, in the form of synthetic fragrance materials such as menthol, citral, cinnamic alcohol, terpineol, and vanillin, and in the form of mixed fragrances blended therefrom; coloring materials such as kuchinashi dye, caramel dye, cochineal dye, annatto dye, safflower dye, β-carotene, and various tar-based synthetic dyes; anticaking agents such as sodium bicarbonate, starch, agar powder, gelatin powder, and crystalline cellulose; gloss-imparting agents such as stearic acid, sugar esters, benzoic acid, and talc; leavening agents such as sodium bicarbonate and glucono delta-lactone; and emulsifiers such as lecithin, sucrose fatty acid esters, glycerine fatty acid esters, and sorbitan fatty acid esters. These may be employed in any combination, and may be employed singly or in mixtures of two or more.

The monatin crystals or sweetener composition of the present invention can be employed in orally consumed products such as foods, beverages, pharmaceutical products, topical pharmaceutical products, and feeds. The formulation thereof is not specifically limited. Examples are powders, granules, cubes, pastes, and liquids. Specific examples are beverages typified by liquid beverages such as fruit drinks, vegetable drinks, cola, carbonated beverages, sports drinks, coffee, black tea, cocoa, and dairy beverages; powdered drinks such as powdered juices; and liquors such as plum wine, medicinal wine, fruit wine, and sake. Further specific examples are foods typified by snacks such as chocolate, cookies, cakes, doughnuts, chewing gum, jelly, pudding, mousse, and Japanese snacks; baked goods such as French bread and croissants; dairy products such as coffee-flavored milk and yogurt; frozen confections such as ice cream and sherbet; powder mixes such as baking mixes and dessert mixes; table sweeteners such as liquid table sweeteners and powdered table sweeteners; dried shellfish products; salted shellfish products; foods boiled down in soy; processed meat and seafood products such as ham, bacon, and sausage; seasonings such as dressings, sauces, soy sauce, miso, sweet sake, ketchup, and steeped barley; spices such as curry powder; processed grain products such as instant noodles; and cereals. Still further specific examples are pharmaceutical products typified by table pharmaceuticals, powdered pharmaceuticals, syrup pharmaceuticals, and drop pharmaceuticals. Still further specific examples are topical pharmaceutical products such as breath fresheners, mouthwashes, toothpastes, and drinks. And still further specific examples are feeds such as pet foods, liquid feeds, and powdered feeds. In particular, from the perspective of maintaining the quality and stability of the sweetness of monatin, those foods, beverages, pharmaceutical products, topical pharmaceutical products, and feeds in which monatin is maintained in crystalline form are desirable; powdered beverages, snacks, powdered mixes, powdered table sweeteners, table pharmaceuticals, powdered pharmaceuticals, and powdered feeds are preferred; and powdered beverages, powdered table sweeteners, and powdered mixes are of greater preference.

The monatin crystals and sweetener composition of the present invention are extremely useful as preventive agents and treatments for metabolic syndromes; preventive agents and treatments for obesity; preventive agents and treatments for diabetes; and cavity-preventing agents. They also have synergistic sweetening effects, synergistic flavoring effects, bitterness-masking effects, and photodecomposition stabilizing effects.

Other features of the invention will become apparent in the course of the following descriptions of exemplary embodiments which are given for illustration of the invention and are not intended to be limiting thereof.

EXAMPLES

Measuring Methods

The various measuring methods will be described first.
Powder X-Ray Diffraction Measuring Method.

1) A 0.5 g quantity of sample was collected and ground for 60 seconds in an agate mortar. The powder obtained was placed on a glass plate, and pressure was applied from above to level the powder. The powder was then immediately placed in a powder X-ray diffractometer and measurements were made under the conditions given below.

2) A PW3050 X-ray diffractometer made by Spectris Co., Ltd. was employed in powder X-ray diffraction measurement with CuKα radiation. Measurements were made under the following conditions: tube: Cu; tube current: 30 mA; tube voltage: 40 kV; sampling width: 0.020°; scan rate: 3°/minute; wavelength: 1.54056 Å; and measurement diffraction angle range (2θ): 4 to 30°.

Measurement program: X'PERT DATA COLLECTION

Analysis program: X'PERT High Score

3) The data obtained were plotted in Excel and characteristic acute maximum peaks were read over the range of 4 to 18°. The diffraction angle error for this method was ±0.2°.
Method of Measuring Monatin Content.

The molar ratio of (2R,4R) monatin and sodium was determined as a concentration ratio by HPLC measurement of the monatin content in a (2R,4R) monatin sodium salt crystal solution of prescribed concentration under the following conditions: Equipment employed.

Pump: LC-9A made by Shimadzu Corporation

Column oven: CTO-10A made by Shimadzu Corporation

Detector: SPD-10A made by Shimadzu Corporation

Autosampler: SIL-9A made by Shimadzu Corporation

Gradientor: LPG-1000 made by Tokyo Rikakikai Co.

Column: CAPCELL PAK C18 TYPE MGII 5 µm 4.6 mm×250 mm made by Shiseido

Column temperature: 40° C.

Detection wavelength: 210 nm

Mobile phase composition: Liquid A 20 mMKH2PO4/acetonitrile=100/5

Liquid B Only acetonitrile

Gradient pattern:

| Time (min) | Liquid A (%) | Liquid B (%) |
|---|---|---|
| 0 | 100 | 0 |
| 15 | 100 | 0 |

-continued

| Time (min) | Liquid A (%) | Liquid B (%) |
|---|---|---|
| 40 | 63 | 37 |
| 45 | 63 | 37 |

Retention time: (2S,4R) Monatin: 11.8 minutes
(2R,4R) Monatin: 15.1 minutes
Quantity introduced: 10 μL
Analysis cycle: 70 min/sample
Standard substance for monatin content measurement:
(2R,4R) Monatin potassium salt monohydrate Molecular weight: 348.4
Monatin content in (2R,4R) monatin sodium salt crystal solution=(292.3/348.4)*(Wstd*Qs)/(Ws*Qstd)*100 (%)
Wstd: Standard substance concentration (mg/mL)
Qstd: Area value of standard substance
Ws: (2R,4R) Monatin sodium salt concentration (mg/mL)
Qs: Area value of (2R,4R) monatin sodium salt
(2R,4R) Monatin free compound Molecular weight: 292.3
Sodium Ion Measurement Method.

The molar ratio of (2R,4R) monatin and sodium was determined as a concentration ratio by measuring the sodium ion concentration in a (2R,4R) monatin sodium salt crystal solution of prescribed concentration by ion chromatography under the following conditions:
Device: Ion chromatograph IC-2001 made by Toso Co., Ltd.
Cation measurement column: TSKgel SuperIC-Cation, inner diameter 4.6 mm, length 150 mm, made by Toso Co., Ltd.
Guard column: TSKguardcolumn SuperIC-C, inner diameter 4.6 mm, length 10 mm, made by Toso Co., Ltd.
Eluant: 2.5 mmol/LHN03±0.5 mmol/L-histidine
Column temperature: 40° C.
Flow rate: 1 mL/minute
Standard solution: Cation standard solution made by Kanto Chemical Co., Inc.
$^1$H-NMR spectral measurement method.
Device: AVANCE400 made by Bruker $^1$H, 400 MHz
Solvent: Heavy water
Temperature Room temperature
Concentration: About 7 weight percent
MS spectral measurement method.
Device: TSQ700 made by Thermo Quest
Measurement mode: ESI mode
Moisture Measurement Method.

The concentration of water in a (2R,4R) monatin sodium salt crystal solution of prescribed concentration was measured by the Karl Fisher method under the following conditions, and the ratio of (2R,4R) monatin and water was calculated from the titration value obtained:
Device: Automatic moisture detector AQV-2000 made by Hiranuma Sangyo Co., Ltd.
Titrant: Hydranal-composite 5 (made by Riedel-deHaen)
Solvent: Methanol
Temperature: Room temperature Manufacturing Example 1

Preparation of (2R,4R) Monatin Monopotassium Salt Monohydrate

In accordance with Example 17 of WO 2003-045914, 10 g of (2R,4R) monatin monoammonium salt crystals were dissolved in water and the solution was processed with cation-exchange resin DIAION PK228 (potassium type, made by Mitsubishi Chemical Corp.). The exiting solution was concentrated, ethanol was added dropwise at 35° C., the crystals were separated, and the mixture was dried under reduced pressure, yielding (2R,4R) monatin monopotassium salt monohydrate crystals (9.3 g).
Melting point: 220.0 to 222.3° C.

Example 1

Preparation of (2R,4R) Monatin Monosodium Salt Hydrate Crystals (A)

A 4 g (11.5 mmol) quantity of the (2R,4R) monatin monopotassium salt monohydrate crystals of Manufacturing Example 1 was dissolved in 40 mL of water, the solution was passed through a column packed with 20 mL of cation-exchange resin DIAION UBK550 (sodium type, made by Mitsubishi Chemical Corp.) for replacement with sodium, and the exiting solution was condensed to 6.4 g. The condensed solution obtained was left standing for 6 hours at 5° C. The crystals were separated from the crystallization solution and washed with 2 mL of cold water. The wet crystals were then dried overnight in a reduced pressure drier at 40° C., yielding 2.28 g (6.4 mmols) of (2R,4R) monatin monosodium salt hydrate crystals (A).
$^1$HNMR (D2O) δ: 1.94-2.01 (q 1H), 2.57-2.61 (q 1H), 2.99-3.03 (d 1H), 3.19-3.23 (d 1H), 3.54-3.57 (q 1H), 7.05-7.17 (m 3H), 7.40-7.42 (m 1H), 7.64-7.66 (m 1H).
ESI-MS: 293.1 (M+H)$^+$, 291.1 (M−H)$^-$
Moisture content: 12.4 wt % (corresponds to 2.5 hydrate)
Sodium content: 6.3 wt %
Characteristic X-ray diffraction peaks (2θ±0.2°, CuKα): 7.7°, 10.9°, 16.7°, and 17.0° (see, FIG. 1)
Diastereomer excess rate: 96.4% de
((2R,4R): (2S,4R)=98.2:1.8)

Example 2

Hydrate Crystallization and Redrying Test

The (2R,4R) monatin monosodium salt hydrate crystals (A) (corresponding to 2.5 hydrate) obtained in Example I were dried for another 24 hours under reduced pressure at 40° C. and cooled overnight to room temperature in a desiccator in the presence of silica gel to obtain the following (2R,4R) monatin monosodium salt hydrate crystals (A):
Moisture content (immediately after drying): 6.9 wt % (corresponding to 1.3 hydrate)
Moisture content (immediately following powder X-ray measurement of crystals stored in desiccator): 8.0 wt % (corresponding to 1.5 hydrate)
Characteristic X-ray diffraction peaks (2θ±0.2°, CuKα): 7.8°, 10.9°, 16.7°, and 17.1° (see, FIG. 4)
This test revealed that a change in the hydrate from 2.5 to 1.5 had almost no effect on the characteristic X-ray diffraction peaks.

Example 3

Water Vapor Adsorption/Desorption Test of (2R,4R) Monatin Monosodium Salt Hydrate Crystals (A)

A water vapor adsorption/desorption curve was plotted for the (2R,4R) monatin monosodium salt hydrate crystals (A)

obtained in Example 1. The measurement conditions were as follows. The measured values are given in FIG. 5.

Device: Automatic vapor adsorption measuring device BELSORP18 made by Bel Japan Inc.
Measurement method: Volumetric gas adsorption method
Measurement conditions:
Adsorbed gas: $H_2O$
Air thermostat temperature (K): 353
Adsorption temperature (K): 298
Saturation vapor pressure (kPa): 3.169
Adsorption cross-sectional area ($nm^2$): 0.125
Maximum adsorption pressure (relative pressure P/PO): desorption: 0.90; adsorption: 0.95
Minimum adsorption pressure (relative pressure P/PO): desorption: 0.10; adsorption: 0.05
Equilibration period: 500 s FIG. 5 shows that the most stable hydrate of (2R,4R) monatin monosodium salt (A) is trihydrate. It also reveals that water of crystallization is gradually released under relatively mild conditions.

Example 4

Preparation of (2R,4R) Monatin Monosodium Salt Monohydrate Crystals (B)

A 40 g (115 mmol) quantity of the (2R,4R) monatin monopotassium salt monohydrate crystals of Manufacturing Example 1 was dissolved in water, the solution was passed through a column packed with 150 mL of cation-exchange resin DIAION UBK550 (sodium type, made by Mitsubishi Chemical Corp.) for replacement with sodium, and the exiting solution was condensed to 99.2 g. While stirring the condensed solution obtained at 50° C., 400 mL of ethanol was added dropwise, and the mixture was calmly stirred overnight at 50° C. The crystals were separated from the crystallization solution and dried overnight in a reduced pressure drier at 40° C., yielding 35.0 g (104 mmols) of (2R,4R) monatin monosodium salt monohydrate crystals (B).

$^1$HNMR (D20) δ: 1.94-2.01 (q 1H), 2.57-2.61 (q 1H), 2.99-3.03 (d 1H), 3.19-3.23 (d 1H), 3.54-3.57 (q 1H), 7.05-7.17 (m 3H), 7.40-7.42 (m 1H), 7.64-7.66 (m 1H).

ESI-MS: 293.1 $(M+H)^+$, 291.1 $(M-H)^-$
Moisture content: 6.6 wt % (corresponds to monohydrate)
Sodium content: 6.8 wt % (corresponds to monosodium)
Characteristic X-ray diffraction peaks (2θ±0.2°, CuKα): 4.7°, 12.4°, 18.8°, and 22.6° (see, FIG. 6)
Sweetness intensity: 2,700-fold (average of values provided by seven panelists relative to 5 percent sucrose aqueous solution)

Example 5

Evaluation of Thermal Stability

The thermal stability of the monatin crystals (B) obtained in Example 4 and the monatin crystals obtained in Comparative Example 1 (Example 14 of WO 2003-045914) was evaluated by the following method.

Evaluation Method.

A 50 mg quantity of the crystals of Example 4 and an identical quantity of the crystals of Comparative Example 1 were placed in separate 4 mL vials and stored at a temperature of 120° C. During this storage, the vials were left open. Following storage periods of 3 hours, 7 hours, and 24 hours, 2 mg of sample was removed and the rate of decomposition of the samples was determined by HPLC. Specifically, decomposition product X was a lactone compound (RT=21 minutes) and decomposition product Y was a lactam compound (RT=26 minutes). The individual area ratios (percentages) were calculated relative to the area of monatin. The results are given in Tables 1 and 2. (For example, for Example 4 at hour 3, the decomposition rates of decomposition products X and Y were calculated as 0.11% and 0.11%, respectively, based on decomposition product X (7432) and decomposition Y (7201).)

TABLE 1

Rate of decomposition over time into the decomposition product X (lactone)

| | Storage time (hr) | | | | |
|---|---|---|---|---|---|
| | 0 | 3 | 7 | 24 | |
| Example 4 | 0% | 0.11% | 0.23% | 0.24% | (a) |
| Comp. Ex. 1 | 0% | 3.38% | 4.64% | 6.67% | (b) |
| Comparison of decomposition rates ((b)/(a)) | — | 30-fold | 21-fold | 27-fold | |

TABLE 2

Rate of decomposition over time into the decomposition product Y (lactam)

| | Storage time (hr) | | | | |
|---|---|---|---|---|---|
| | 0 | 3 | 7 | 24 | |
| Example 4 | 0% | 0.11% | 0.21% | 0.38% | (a) |
| Comp. Ex. 1 | 0% | 2.08% | 3.63% | 7.46% | (b) |
| Comparison of decomposition rates ((b)/(a)) | — | 19-fold | 17-fold | 20-fold | |

This test revealed that the rate of decomposition (at 24 hours) of the monatin crystals of Comparative Example 1 into decomposition product X (lactone compound) was 27-fold, and the rate of decomposition (at 24 hours) into decomposition product Y (lactam compound) was 20-fold, those of the monatin crystals of Example 4. The test also revealed that the thermal stability of the (2R,4R) monatin monosodium salt monohydrate crystals (B) of the present invention was drastically better. FIGS. 8 and 9 are plots of the rates of decomposition over time into decomposition product X (lactone compound) and Y (lactam compound) for Example 4 and Comparative Example 1; the differences are immediately apparent.

Formulation Example 1

Table Sweetener

TABLE

| | Weight percent. |
|---|---|
| Hydrate crystals (A) described in Example 1 | 0.12 |
| Erythritol | 20 |
| Reduced maltose | remainder |
| Total | 100 |

A table sweetener was prepared by mixing the above powders. When tested by addition to coffee, it exhibited a good quality of sweetness similar to that of sugar. It was also tested by being sprinkled on hot cakes, producing a pleasant taste sensation without creating a gritty sensation on the tip of the tongue, dissolving well in the mouth, having a good initial sweetness, and exhibiting sweetness of the same good quality as granulated sugar.

INDUSTRIAL APPLICABILITY (2R,4R) Monatin monosodium salt hydrate crystals ((A) and (B)) make it possible to provide stable sodium salt crystals of monatin. The utility and various physical properties of these stereoisomers as sweeteners have been clarified. They also make it possible to provide orally consumed products, such as foods, beverages, pharmaceutical products, topical pharmaceutical products, and feeds that contain general-purpose, stable, and safe monatin sodium salt crystals, which is of great significance.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. Crystalline (2R,4R) monatin monosodium salt hydrate, selected from the group consisting of:
    (A) crystalline (2R,4R) monatin monosodium salt hydrate having characteristic X-ray diffraction peaks at angles of diffraction ($2\theta\pm0.2°$, CuK$\alpha$) of 7.7°, 10.9°, 16.7°, and 17.0°; and
    (B) crystalline (2R,4R) monatin monosodium salt hydrate having characteristic X-ray diffraction peaks at angles of diffraction ($2\theta\pm0.2°$, CuK$\alpha$) of 4.7°, 12.4°, 18.8°, and 22.6°.

2. Crystalline (2R,4R) monatin monosodium salt hydrate according to claim 1, having characteristic X-ray diffraction peaks at angles of diffraction ($2\theta\pm0.2°$, CuK$\alpha$) of 7.7°, 10.9°, 16.7°, and 17.0°.

3. Crystalline monatin, which comprises crystalline (2R,4R) monatin monosodium salt hydrate according to claim 2.

4. Crystalline (2R,4R) monatin monosodium salt hydrate according to claim 2, which has an enantiomer excess rate of 10 to 100% ee.

5. Crystalline (2R,4R) monatin monosodium salt hydrate according to claim 2, which has a diastereomer excess rate of 10 to 100% de.

6. Crystalline (2R,4R) monatin monosodium salt hydrate according to claim 2, wherein the sweetness intensity thereof is 200-fold or more that of a 5 percent sucrose aqueous solution.

7. Crystalline (2R,4R) monatin monosodium salt hydrate according to claim 2, wherein the chemical purity thereof is 50 to 100 weight percent.

8. Crystalline monatin according to claim 3, wherein the enantiomer excess rate of the (2R,4R) monatin monosodium salt hydrate crystals is 10 to 100% ee.

9. Crystalline monatin according to claim 3, wherein the diastereomer excess rate of the (2R,4R) monatin monosodium salt hydrate crystals is 10 to 100% de.

10. Crystalline monatin according to claim 3, wherein the sweetness intensity thereof is 200-fold or more that of a 5 percent sucrose aqueous solution.

11. Crystalline monatin according to claim 3, wherein the chemical purity thereof is 50 to 100 weight percent.

12. An orally consumed product, comprising crystalline (2R,4R) monatin monosodium salt hydrate according to claim 2.

13. An orally consumed product, comprising crystalline monatin according to claim 3.

14. A method for making an orally consumed product, comprising adding crystalline (2R,4R) monatin monosodium salt hydrate according to claim 2 to at least one ingredient for an orally consumed product.

15. A method for making an orally consumed product, comprising adding crystalline monatin according to claim 3 to at least one ingredient for an orally consumed product.

16. A method for making crystalline (2R,4R) monatin monosodium salt hydrate, having characteristic X-ray diffraction peaks at angles of diffraction ($2\theta\pm0.2°$, CuK$\alpha$) of 7.7°, 10.9°, 16.7°, and 17.0°, said method comprising:
    allowing an aqueous solution containing a high concentration of (2R,4R) monatin monosodium salt to stand or subjecting it to stirring precipitation to obtain said crystals.

17. A method for making crystalline (2R,4R) monatin monosodium salt hydrate, having characteristic X-ray diffraction peaks at angles of diffraction ($2\theta\pm0.2°$, CuK$\alpha$) of 4.7°, 12.4°, 18.8°, and 22.6°, said method comprising:
    concentrating an aqueous solution (2R,4R) monatin monosodium salt, to obtain a concentrated solution having a concentration of (2R,4R) monatin monosodium salt of 20 to 60 weight percent;
    introducing a water-miscible solvent into said concentrated solution, to obtain a mixture; and
    allowing said mixture to stand or inducing crystallization by stirring.

18. Crystalline (2R,4R) monatin monosodium salt hydrate according to claim 1, having characteristic X-ray diffraction peaks at angles of diffraction ($2\theta\pm0.2°$, CuK$\alpha$) of 4.7°, 12.4°, 18.8°, and 22.6°.

19. Crystalline (2R,4R) monatin monosodium salt hydrate according to claim 18, which has an enantiomer excess rate of 10 to 100% ee.

20. Crystalline (2R,4R) monatin monosodium salt hydrate according to claim 18, which has a diastereomer excess rate of 10 to 100% de.

21. Crystalline (2R,4R) monatin monosodium salt hydrate according to claim 18, wherein the sweetness intensity thereof is 200-fold or more that of a 5 percent sucrose aqueous solution.

22. Crystalline (2R,4R) monatin monosodium salt hydrate according to claim 18, wherein the chemical purity thereof is 50 to 100 weight percent.

23. Crystalline monatin, which comprises crystalline (2R,4R) monatin monosodium salt hydrate according to claim 18.

24. Crystalline monatin according to claim 23, wherein the enantiomer excess rate of the (2R,4R) monatin monosodium salt hydrate crystals is 10 to 100% ee.

25. Crystalline monatin according to claim 23, wherein the diastereomer excess rate of the (2R,4R) monatin monosodium salt hydrate crystals is 10 to 100% de.

26. Crystalline monatin according to claim 23, wherein the sweetness intensity thereof is 200-fold or more that of a 5 percent sucrose aqueous solution.

27. Crystalline monatin according to claim 23, wherein the chemical purity thereof is 50 to 100 weight percent.

28. An orally consumed product, comprising crystalline (2R,4R) monatin monosodium salt hydrate according to claim 18.

29. An orally consumed product, comprising crystalline monatin according to claim 23.

30. A method for making an orally consumed product, comprising adding crystalline (2R,4R) monatin monosodium salt hydrate according to claim 18 to at least one ingredient for an orally consumed product.

31. A method for making an orally consumed product, comprising adding crystalline according to claim 23 to at least one ingredient for an orally consumed product.

* * * * *